(12) United States Patent
Currier et al.

(10) Patent No.: US 11,236,806 B2
(45) Date of Patent: Feb. 1, 2022

(54) STEERABLE MEDICAL DEVICE HAVING A CONTROL MEMBER HOLDING MECHANISM

(71) Applicant: Boston Scientific Scimed, Inc., Maple Grove, MN (US)

(72) Inventors: Jonathan M. Currier, Nashua, NH (US); James R. Black, Medina, OH (US); Paul K. Barner, Waltham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/815,193

(22) Filed: Mar. 11, 2020

(65) Prior Publication Data
US 2020/0208718 A1 Jul. 2, 2020

Related U.S. Application Data

(63) Continuation of application No. 14/203,804, filed on Mar. 11, 2014, now Pat. No. 10,619,714.
(Continued)

(51) Int. Cl.
*A61B 1/005* (2006.01)
*F16H 19/06* (2006.01)
(Continued)

(52) U.S. Cl.
CPC ......... *F16H 19/0672* (2013.01); *A61B 1/005* (2013.01); *A61B 1/0052* (2013.01);
(Continued)

(58) Field of Classification Search
CPC ..... A61B 1/005; A61B 1/0051–1/0053; A61B 1/0055–1/0058; A61B 1/008;
(Continued)

(56) References Cited

U.S. PATENT DOCUMENTS 5,167,221 A * 12/1992 Chikama .............. A61B 1/0052
600/149
5,454,827 A * 10/1995 Aust ...................... A61B 17/29
600/564
(Continued)

*Primary Examiner* — Ryan N Henderson
*Assistant Examiner* — Pamela F Wu
(74) *Attorney, Agent, or Firm* — Bookoff McAndrews, PLLC

(57) ABSTRACT

Embodiments of the present disclosure include a medical device. The medical device may include an elongate member, a first control member and a second control member each coupled to a distal end of the elongate member, an actuator coupled to the first control member and the second control member and configured to selectively move the first control member and the second control member to steer the elongate member, and a holding mechanism deflecting a path of the first control member from the actuator to the distal end of the elongate member and a path of the second control member from the actuator to the distal end of the elongate member. The holding mechanism may be configured to apply tension on one of the first control member and the second control member as the other is moved to steer the elongate member.

20 Claims, 5 Drawing Sheets

Related U.S. Application Data

(60) Provisional application No. 61/779,405, filed on Mar. 13, 2013.

(51) Int. Cl.
*A61M 25/01* (2006.01)
*A61B 17/00* (2006.01)

(52) U.S. Cl.
CPC ....... *A61B 1/0057* (2013.01); *A61M 25/0136* (2013.01); *A61B 2017/00327* (2013.01); *A61M 25/0147* (2013.01); *Y10T 74/18832* (2015.01)

(58) Field of Classification Search
CPC .......... A61B 1/00066; A61B 2017/003; A61B 2017/003118; A61B 2017/00323; A61B 2017/00327; A61M 25/0133; A61M 25/0136; A61M 25/0147; F16H 19/0672; Y10T 74/18832; Y10T 2017/00292; Y10T 17/068
USPC ............. 74/89.2, 89.21, 89.22; 600/149–150
See application file for complete search history.

(56) References Cited

U.S. PATENT DOCUMENTS

| | | | |
|---|---|---|---|
| 8,808,166 B2 | 8/2014 | Hosaka | |
| 2005/0277874 A1* | 12/2005 | Selkee | A61M 25/0147 604/95.04 |
| 2010/0069834 A1* | 3/2010 | Schultz | A61M 25/0147 604/95.04 |
| 2012/0046522 A1 | 2/2012 | Naito | |
| 2012/0302832 A1* | 11/2012 | Inada | A61B 1/00039 600/118 |
| 2013/0047757 A1 | 2/2013 | Okamoto et al. | |
| 2013/0060088 A1* | 3/2013 | Okamoto | A61B 1/00066 600/146 |

* cited by examiner

STEERABLE MEDICAL DEVICE HAVING A CONTROL MEMBER HOLDING MECHANISM

CROSS-REFERENCE TO RELATED APPLICATIONS

This application is a continuation of U.S. application Ser. No. 14/203,804, filed on Mar. 11, 2014, which claims the benefit of priority from U.S. Provisional Application No. 61/779,405, filed on Mar. 13, 2013, the entirety of each of which is incorporated by reference herein.

FIELD OF THE DISCLOSURE

Embodiments of the present disclosure include medical devices, and more particularly, medical devices including a holding mechanism for applying tension to control members, and related methods of using such medical devices.

BACKGROUND OF THE DISCLOSURE

Generally, steerable medical devices, such as certain endoscopes, ureteroscopes, and other scopes, catheters, and guides, may include a flexible shaft configured to be deflected or maneuvered to facilitate guidance through tortuous or furcated anatomical passageways. In order to effect and control the steering of the shaft, a plurality of control cables or wires may run the length of the medical device and may be operably connected to a distal end of the shaft. The proximal ends of the control cables may be coupled to a suitable actuator, and the actuator may proximally retract a control cable to bend the shaft in a desired direction.

As one control cable is proximally retracted, an opposing control cable is released or slackened. The slacked control cable may, however, be prone to uncontrollable movement within the medical device, and particularly, within the shaft. Such movement may cause inadvertent contact with other components of the medical device and/or snagging of the control cable, which may ultimately result in damage to the control cables and/or the other components.

Accordingly, the medical device and related methods of the present disclosure are directed to improvements in the existing technology.

SUMMARY OF THE DISCLOSURE

In accordance with an embodiment, a medical device may include an elongate member, a first control member and a second control member each coupled to a distal end of the elongate member, an actuator coupled to the first control member and the second control member and configured to selectively move the first control member and the second control member to steer the elongate member, and a holding mechanism deflecting a path of the first control member from the actuator to the distal end of the elongate member and a path of the second control member from the actuator to the distal end of the elongate member, wherein the holding mechanism is configured to apply tension on one of the first control member and the second control member as the other is moved to steer the elongate member.

Various embodiments of the disclosure may include one or more of the following aspects: the holding mechanism may include a first arm and a second arm, wherein the first arm may deflect the path of the first control member, and the second arm may deflect the path of the second control member; the first arm may include a first hooked segment, and the second arm may include a second hooked segment, wherein the first control member may extend through the first hooked segment, and the second control member may extend through the second hooked segment; the holding mechanism may include a connecting segment, wherein the first arm and the second arm may be angled towards the connecting segment such that the first hooked segment and the second hooked segment may face the connecting segment; a handle coupled to the elongate member, wherein the handle may house the first control member, the second control member, and the holding mechanism; the holding mechanism may be affixed to an inner surface of the handle; the first arm may be configured to bend when the first control member is moved to steer the elongate member, and the second arm may be configured to bend when the second control member is moved to steer the elongate member; when the first control member is moved to steer the elongate member, the first arm may be configured to bend towards a longitudinal axis of the elongate member, and wherein, when the second control member is moved to steer the elongate member, the second arm may be configured to bend towards the longitudinal axis of the elongate member; the first arm may be longer than a length of the second arm; and the holding mechanism may comprise a resilient material.

In accordance with another embodiment, a medical device may include an elongate member including a longitudinal axis, a first control member and a second control member each coupled to a distal end of the elongate member, an actuator coupled to the first control member and the second control member and configured to selectively move the first control member and the second control member to steer the elongate member, and a holding mechanism including a first arm and a second arm, wherein the first arm is configured to apply tension on the first control member, and the second arm is configured to apply tension on the second control member, wherein, when the actuator moves the first control member to steer the elongate member, the first arm is configured to bend towards the longitudinal axis of the elongate member.

Various embodiments of the disclosure may include one or more of the following aspects: when the actuator moves the second control member to steer the elongate member, the second arm may be configured to bend towards the longitudinal axis of the elongate member; the actuator may be configured to proximally retract the first control member and distally advance the second control member to steer the elongate member in a first direction; the actuator may be configured to proximally retract the second control member and distally advance the first control member to steer the elongate member in a second direction; proximal retraction of the first control member may cause the first arm to bend towards the longitudinal axis of the elongate member, and wherein proximal retraction of the second control member may cause the second arm to bend towards the longitudinal axis of the elongate member; and the first arm may include a first hooked segment through which the first control member extends, and wherein the second arm may include a second hooked segment through which the second control member extends.

In accordance with yet another embodiment, a medical device may include an elongate member, a first control member and a second control member each coupled to a distal end of the elongate member, an actuator coupled to the first control member and the second control member and configured to selectively move the first control member and the second control member to steer the elongate member, and a holding mechanism including a first arm configured to apply tension on the first control member and having a first hooked segment, and a second arm configured to apply tension on the second control member and having a second hooked segment, wherein the first control member extends through the first hooked segment, and the second control member extends through the second hooked segment.

Various embodiments of the disclosure may include one or more of the following aspects: when the actuator moves the first control member to steer the elongate member, the first control member may be configured to apply a force on the member, the second control member may be configured to apply a force on the second hooked segment to bend the second arm towards the longitudinal axis of the elongate member; and the first arm may be configured to apply tension to the first control member by deflecting a path of the first control member, and the second arm may be configured to apply tension to the second control member by deflecting a path of the second control member.

DETAILED DESCRIPTION

Reference will now be made in detail to exemplary embodiments of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary disclosed medical device. When used herein, "proximal" refers to a position relatively closer to the exterior of the body or closer to the user of the medical device. In contrast, "distal" refers to a position relatively further away from the user of the medical device or closer to the interior of the body.

Figure 1:
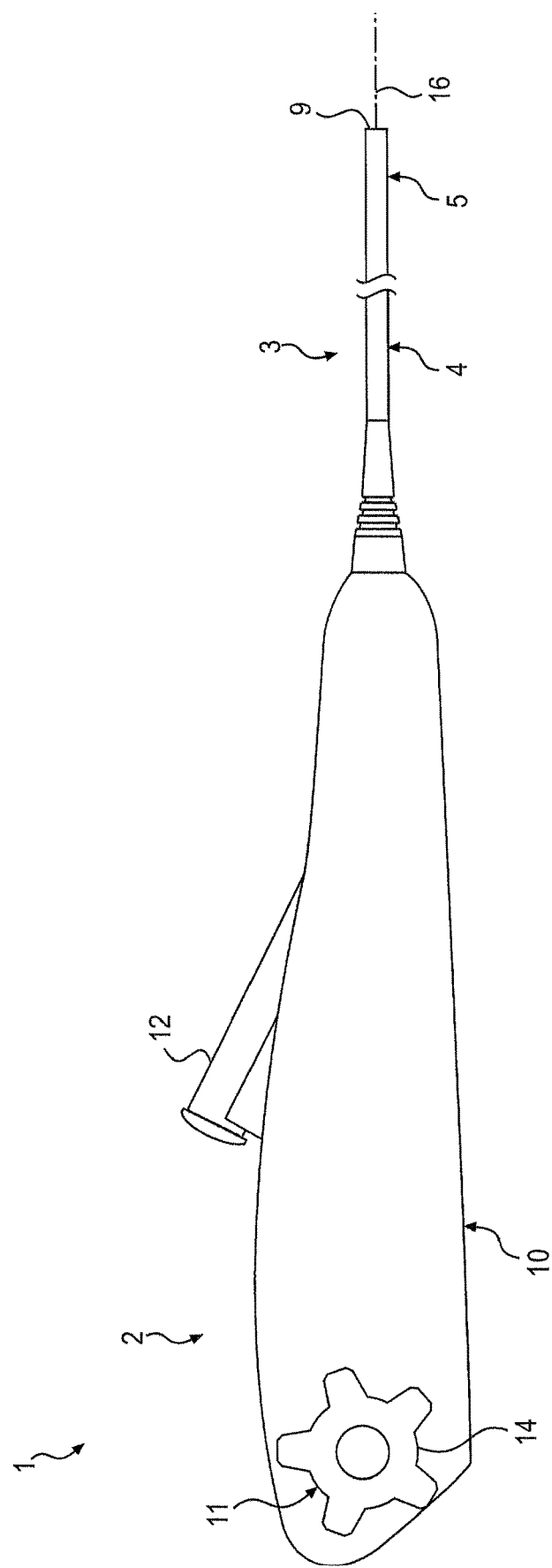
FIG. 1 illustrates a medical device, according to an exemplary disclosed embodiment.

FIG. 1 illustrates a medical device 1, according to an exemplary embodiment. Medical device 1 may be any device configured to allow an operator to access internal body anatomies of a patient, as well as optionally to view those anatomies and/or to deliver medical instruments, such as, for example, biopsy forceps, graspers, baskets, snares, probes, scissors, retrieval devices, lasers, and other tools, into the patient's body. Medical device 1 may be inserted into a variety of body lumens and/or cavities, such as, for example, any portion of a urinary tract including a ureter, a gastrointestinal lumen including an esophagus, a vascular lumen, an airway, and the like.

For the purposes of the present disclosure, medical device 1 may be a an endoscope. Other types of devices suitable for use in connection with the present disclosure include, as examples, a ureteroscope, a hysteroscope, a uteroscope, a bronchoscope, a cystoscope, a catheter, a guide tube, and the like.

Endoscope 1 may include a handle assembly 2 and an elongate member 3 operably connected to handle assembly 2. Elongate member 3 may be configured to be at least partially inserted into a body of a patient. Elongate member 3 may be flexible, or may include one or more portions that are flexible, to allow elongate member 3 to be maneuvered and steered within the body and traverse tortuous anatomical lumens. For instance, elongate member 3 may be uniformly flexible or may include a plurality of portions having varying degrees of flexibility or rigidity. Elongate member 3 may include a proximal portion 4, a distal portion 5, and a medial portion disposed between proximal portion 4 and distal portion 5.

Handle assembly 2 may include a handle housing 10 to which a steering mechanism 11 and one or more ports 12 may be operably coupled. Port 12 may provide access to one or more channels extending through elongate member 3. For example, port 12 may provide access for one or more medical tools to a working channel extending through elongate member 3 and out a tip 9 of elongate member 3. Additionally, port 12 may provide access through the working channel for a suitable fluid, such as water or gas, for, as examples, irrigation, insufflation, and/or suction purposes.

Steering mechanism 11 may be configured to control the steering and deflection of distal portion 5 of elongate member 3. Steering mechanism 11 may include an actuator 14 configured to control deflection of distal portion 5 between a substantially linear configuration and a curved, angled, or bent configuration. Distal portion 5 may be moved to a variety of different curved, angled, or bent configurations in a variety of different directions relative to a longitudinal axis 16 of elongate member 3.

Actuator 14 may include a rotatable knob or dial and may be actuated to deflect elongate member 3. For example, rotating the knob counterclockwise or clockwise may cause distal portion 5 to deflect in a first direction or a second direction of a first plane (i.e., up and down relative to longitudinal axis 16). In certain other embodiments, actuator 14 may include a deflectable lever configured to be actuated up and down or side-to-side relative to handle housing 10. Actuating the deflectable lever may cause distal portion 5 to deflect in the first direction or the second direction.

Although not shown, it should be appreciated that steering mechanism 11 may include a second actuator configured to deflect distal portion 5 in a first direction and a second direction of a second plane different than the first plane (i.e., side-to-side relative to longitudinal axis 16). Accordingly, steering mechanism 11 may provide four-way steering of distal portion 5 of elongate member 3. It should also be appreciated, however, that steering mechanism 11 may provide less or greater than four-way steering of distal portion 5, depending on, for example, the volume and/or the shape of the internal body anatomies which may be traversed by elongate member 3.

Figure 2:
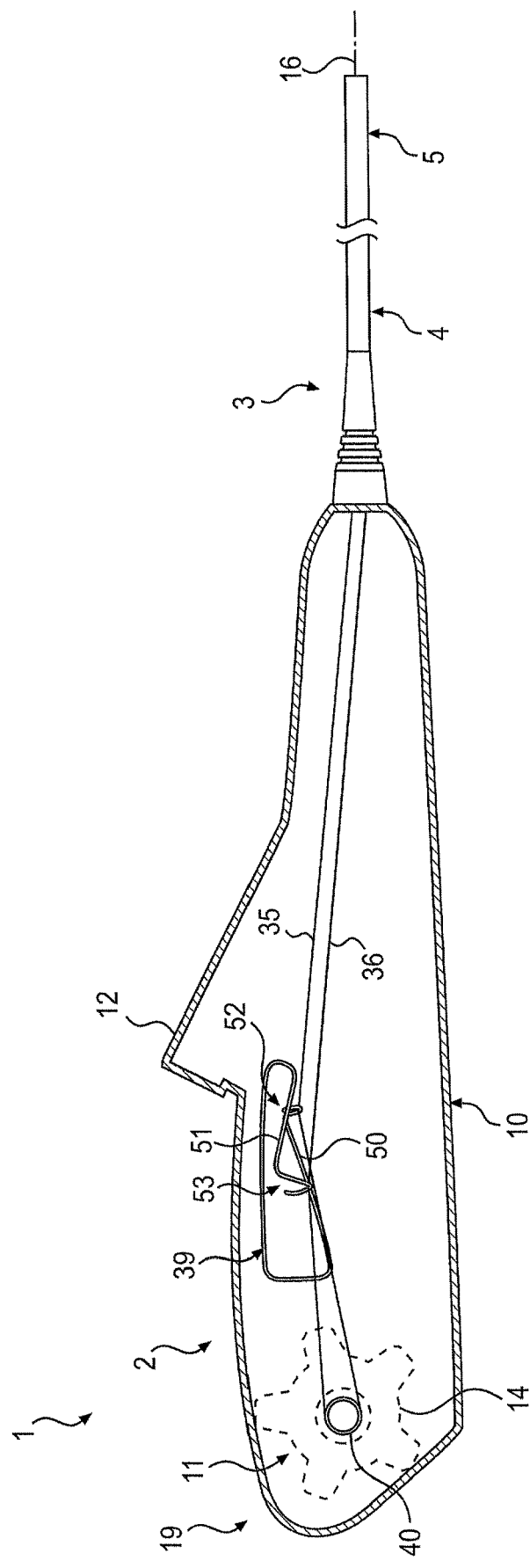
FIG. 2 illustrates a plan view of parts of a handle assembly of the medical device of FIG. 1 in a linear configuration, according to an exemplary disclosed embodiment.

FIG. 2 illustrates a plan view of inner parts of handle assembly 2 of endoscope 1 with distal portion 5 of elongate member 3 in the linear configuration. Handle assembly 2 may include handle housing 10 comprising two half-portions (only one half-portion shown in FIG. 2) joined together by appropriate removable fasteners, such as screws and pins, or by appropriate non-removable fastening techniques, such as heat bonding. Handle housing 10 may house steering mechanism 11. Although not shown, it should also be appreciated that handle housing 10 may house one or more additional components of endoscope 1, including, as examples, an illumination system and an imaging system.

Steering mechanism 11 may be housed within handle housing 10 at a proximal end 19 of handle assembly 2. As shown in FIG. 2, in addition to actuator 14, steering mechanism 11 may include a first control member 35, a second control member 36, and a control member holding mechanism 39. Control members 35, 36 may each be coupled to elongate member 3 at or near tip 9 and may extend through elongate member 3 and handle housing 10 to actuator 14. Control members 35, 36 may be coupled to elongate member 3 on opposite sides of elongate member 3. It should be appreciated that control members 35, 36 may include any suitable coupling device, such as, for example, a wire, a cable, a rod, a filament, a braided member, or a hollow tube.

The proximal ends of control members 35, 36 may be connected to a spool 40 of actuator 14. In some embodiments, the proximal ends of control members 35, 36 may be connected on opposite sides of the circumference of spool 40 and spaced apart along the length of spool 40. In certain other embodiments, control members 35, 36 may be looped one or more times around the circumference of spool 40. Spool 40 in turn may be connected to the rotatable knob of actuator 14. Accordingly, rotating the knob counterclockwise may proximally retract control member 36 and distally advance control member 35, thus causing distal portion 5 of elongate member 3 to deflect in the first direction. Rotating the knob clockwise may proximally retract control member 35 and distally advance control member 36, thus causing distal portion 5 to deflect in the second direction.

Control member holding mechanism 39 may be positioned proximate actuator 14. Holding mechanism 39 may include a first arm 50 and a second arm 51. First arm 50 may include a first hooked segment 52 configured to support control member 35, and second arm 51 may include a second hooked segment 53 configured to support control member 36. As will be described in more detail below, holding mechanism 39 may be configured to retain and apply tension to control members 35, 36.

Figure 3:
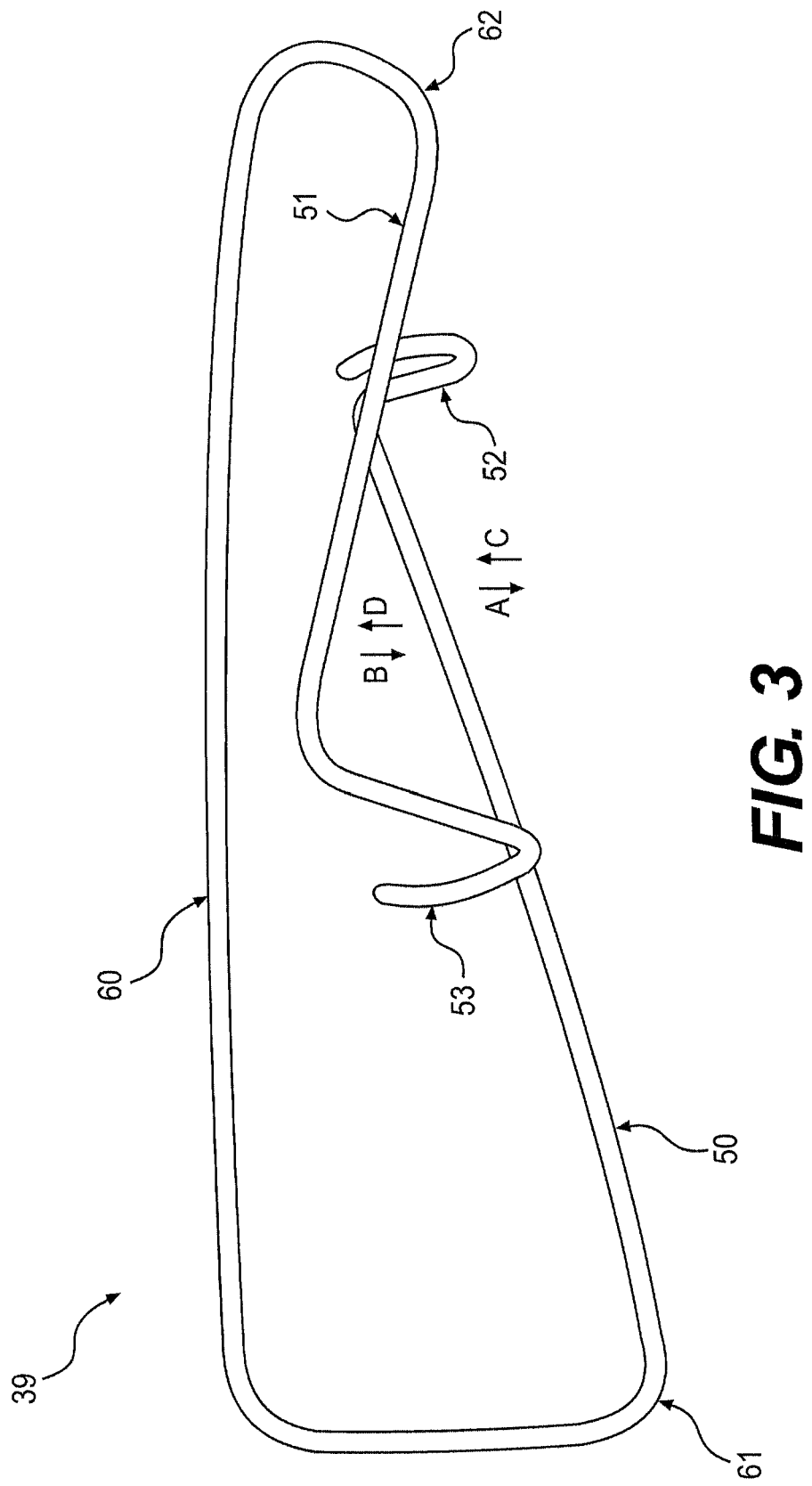
FIG. 3 illustrates a perspective view of a control member holding mechanism of the medical device of FIG. 1, according to an exemplary disclosed embodiment.

FIG. 3 illustrates a perspective view of holding mechanism 39 without endoscope 1. Holding mechanism 39 may be a unitary piece of any suitable resilient material, such as, for example, nitinol or stainless steel. In a normal configuration, one or both of first arm 50 and second arm 51 may be in its naturally biased state (i.e., in the positions shown in FIG. 3). That is, when first arm 50 or second arm 51 is in the normal configuration, no force is applied on first arm 50 or second arm 51 sufficient to bend first arm 50 or second arm 51.

First arm 50 and second arm 51 may be configured, however, to deflect from the normal configuration if a force sufficient to overcome the biasing force of either first arm 50 or second arm 51 is applied on first arm 50 or second arm 51. For example, proximal retraction of control member 35 may apply sufficient force onto first arm 50 to bend first arm 50 downwards, as indicated by arrow A. Similarly, proximal retraction of control member 36 may apply sufficient force onto second arm 51 to bend second arm 51 downwards, as indicated by arrow B. Distal advancement of control member 35 may release the force on first arm 50, and the biasing force of first arm 50 may resiliently deflect first arm 50 upwards back to the normal configuration, as indicated by arrow C. Likewise, distal advancement of control member 36 may release the force on second arm 51, and the biasing force of second arm 51 may resiliently deflect second arm 51 upwards back to the normal configuration, as indicated by arrow D.

As shown in FIG. 3, holding mechanism 39 may include a connecting segment 60 from which first arm 50 and second arm 51 extend. Connecting segment 60 may be connected to an inner wall of handle housing 10 by any suitable means, such as, for example, adhesives, welding, or mechanical fasteners. First arm 50 may extend from connecting segment 60 and may include a first curved portion 61 to direct first hooked segment 52 towards connecting segment 60. That is, first arm 50 may be angled towards connecting segment 60. In addition, first arm 50 may bend at first curved portion 61 upon proximal retraction of control member 35. Similarly, second arm 51 may extend from connecting segment 60 and may include a second curved portion 62 to direct second hooked segment 53 towards connecting segment 60. Second arm 51 may be angled towards connecting segment 60, and may bend at second curved portion 62 upon proximal retraction of control member 36.

Moreover, first arm 50 may include a length larger than a length of second arm 51. First hooked segment 52 may therefore be positioned between second hooked segment 53 and second curved portion 62, and second hooked segment 53 may be positioned between first hooked segment 52 and first curved portion 61. Accordingly, first hooked segment 52 and second hooked segment 53 may be prevented from contacting and interfering with each other as either of first arm 50 or second arm 51 is deflected.

First arm 50 and second arm 51 may also be configured to provide space between control member 35 and control member 36. For example, and as shown in FIGS. 2-5, second arm 51 may angle away from first arm 50 at second curved portion 62. For example, second arm 51 may be directed out of the plane of the page in FIGS. 2-5. As such, first hooked segment 52 and second hooked segment 53 may be spaced apart, and consequently, control members 35, 36 extending though first and second hooked segments 52, 53 may also be spaced apart. Therefore, contact and interference between control members 35, 36 during actuation of actuator 14 may be prevented.

With reference back to FIG. 2, holding mechanism 39 may be positioned within handle housing 10 such that first and second hooked segments 52, 53 may be offset from longitudinal axis 16 of elongate member 3. For example, holding mechanism 39 may be disposed above elongate member 3 (and longitudinal axis 16) and proximate port 12. As alluded to above, control member 35 may extend through first hooked segment 52, and first arm 50 may apply tension to control member 35 by raising a portion of control member 35 above longitudinal axis 16 of elongate member 3 and the connection point of control member 35 at distal portion 5. Similarly, control member 36 may extend through second hooked segment 53, and second arm 51 may apply tension to control member 36 by raising a portion of control member 36 above longitudinal axis 16 of elongate member 3 and the connection point of control member 36 at distal portion 5. Therefore, first and second arms 50, 51 of holding mechanism 39 may remove slack on control members 35, 36 by deflecting the paths of control members 35, 36 between actuator 14 and distal portion 5 of elongate member 3.

In accordance with a first embodiment, when distal portion 5 of elongate member 3 is in the linear (unbent) configuration, holding mechanism 39 may apply tension to control members 35, 36 while first arm 50 and second arm 51 are in the normal configuration. First arm 50 may raise a portion of control member 35 above longitudinal axis 16 to apply tension to control member 35, but control member 35 may not apply a force onto first arm 50 sufficient to overcome the biasing force of first arm 50 and deflect first arm 50 downwards. In addition, second arm 51 may raise a portion of control member 36 above longitudinal axis 16 to apply tension to control member 36, but control member 36 may not apply a force onto second arm 51 sufficient to overcome the biasing force of second arm 51 and deflect second arm 51 downwards.

In accordance with a second embodiment, when distal portion 5 of elongate member 3 is in the linear (unbent) configuration, holding mechanism 39 may apply tension to control members 35, 36 while first arm 50 and second arm 51 are partially deflected from the normal configuration. In such an embodiment, first arm 50 may raise a portion of control member 35 above longitudinal axis 16 to apply tension to control member 35. The tension on control member 35, however, may apply a force onto first arm 50 sufficient to partially overcome the biasing force of first arm 50 and slightly bend first arm 50 towards longitudinal axis 16. Similarly, second arm 51 may raise a portion of control member 36 above longitudinal axis 16 to apply tension to control member 36. The tension on control member 36, however, may apply a force onto second arm 51 sufficient to partially overcome the biasing force of second arm 51 and slightly bend second arm 51 towards longitudinal axis 16. First arm 50 and second arm 51 may be partially deflected from the normal configuration in the second embodiment due to a higher degree of force applied onto first arm 50 and second arm 51 by control members 35, 36 relative to the first embodiment. Such a higher degree of force may be caused by, for example, a higher position of holding mechanism 39 relative to longitudinal axis 16 and/or shorter lengths of control members 35, 36 (and consequently, less pre-existing slack on control members 35, 36).

Figure 4:
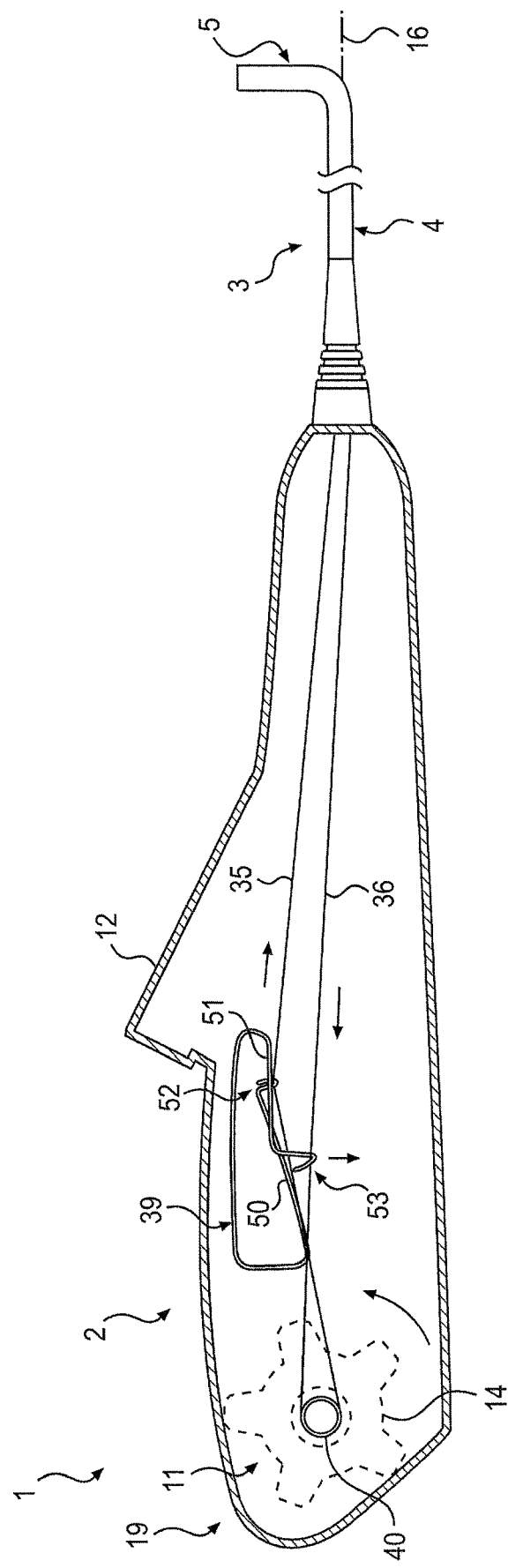
FIG. 4 illustrates a plan view of parts of a handle assembly of the medical device of FIG. 1 steered in a first direction, according to an exemplary disclosed embodiment.

FIG. 4 illustrates a plan view of inner parts of handle assembly 2 when distal portion 5 of elongate member 3 is deflected in the first direction. Rotating the knob of actuator 14 counterclockwise may proximally retract control member 36 and distally advance control member 35, thus causing elongate member 3 to deflect in the first direction (i.e., up relative to longitudinal axis 16). Moreover, as control member 36 is proximally retracted, control member 36 may apply a force onto second hooked segment 53, which may cause second arm 51 to bend. The proximal retraction of control member 36 may deflect second hooked segment 53 downward towards longitudinal axis 16 of elongate member 3, which may pull second arm 51 downward towards longitudinal axis 16 of elongate member 3. Although not illustrated, it should be appreciated that in certain embodiments, second hooked segment 53 may be curved such that an apex of second hooked segment 53 substantially points towards actuator 14 in the normal configuration. Accordingly, second hooked segment 53 may be substantially directed towards the direction of force applied onto control member 36, thus facilitating eased bending of second arm 51.

In accordance with the first embodiment, first arm 50 may remain in the normal configuration when distal portion 5 of elongate member 3 is steered to the first direction. While second arm 51 is deflected upon proximal retraction of control member 36, first arm 50 may remain substantially stationary and may not significantly deflect or bend from the normal configuration. Rotating the knob counterclockwise may distally advance control member 35 through first hooked segment 52. Distal advancement of control member 35 may not, however, apply a force onto first hooked segment 52 sufficient to bend first arm 50, since some slack may occur in control member 35. Control member 35 may be pushed through first hooked segment 52 without pulling down on first arm 50.

By remaining in the normal configuration, first arm 50 may maintain some tension along control member 35 as control member 36 is proximally retracted. Because first arm 50 may remain in the normal configuration, the path of control member 35 may be maintained above longitudinal axis 16 of elongate member 3, and control member 35 may be held substantially taut against first hooked segment 52. When desired, elongate member 3 may be steered back to the linear configuration shown in FIG. 2 by rotating the knob clockwise.

In accordance with the second embodiment, first arm 50 may resiliently deflect towards the normal configuration when distal portion 5 of elongate member 3 is steered to the first direction. Rotating the knob counterclockwise may proximally retract control member 36 and distally advance control member 35 through first hooked segment 52. Proximal retraction of control member 36 may further deflect second arm 51 downward towards longitudinal axis 16, while distal advancement of control member 35 may release some of the force applied on first arm 50 by control member 35. The slight release in force may cause first arm 50 to resiliently deflect back towards the normal configuration. It should be appreciated that first arm 50 may deflect to the normal configuration or any position between the normal configuration and the slightly bent configuration discussed above.

While first arm 50 may deflect towards the normal configuration, first arm 50 may retain the path of control member 35 above longitudinal axis 16 of elongate member 3 such that tension along control member 35 may be maintained. Moreover, control member 35 may be held substantially taut against first hooked segment 52.

Figure 5:
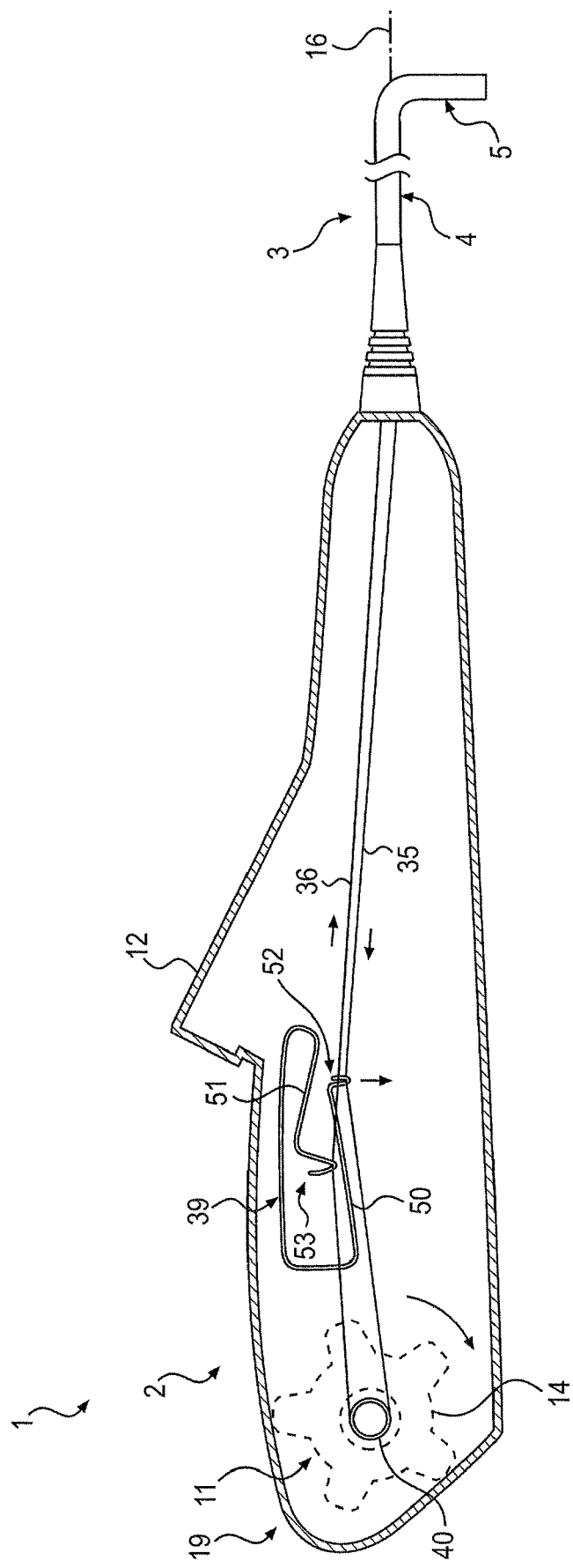
FIG. 5 illustrates a plan view of parts of a handle assembly of the medical device of FIG. 1 steered in a second direction, according to an exemplary disclosed embodiment.

FIG. 5 illustrates a plan view of inner parts of handle assembly 2 when distal portion 5 of elongate member 3 is deflected in the second direction. Rotating the knob of actuator 14 clockwise may proximally retract control member 35 and distally advance control member 36, thus causing elongate member 3 to deflect in the second direction (i.e., down relative to longitudinal axis 16). As control member 35 is proximally retracted, control member 35 may apply a force onto first hooked segment 52, which may cause first arm 50 to bend. Control member 35 may be deflected downward towards longitudinal axis 16 of elongate member 3, which may pull first arm 50 downward towards longitudinal axis 16 of elongate member 3. Although not illustrated, it should be appreciated that in certain embodiments, an apex of first hooked segment 52 may substantially point towards actuator 14 in the normal configuration to facilitate eased bending of first arm 50.

In accordance with the first embodiment, second arm 51 may remain in the normal configuration when distal portion 5 of elongate member 3 is steered to the second direction. While first arm 50 is deflected by proximal retraction of control member 35, second arm 51 may remain substantially stationary and may not significantly deflect or bend from the normal configuration. Rotating the knob clockwise may also distally advance control member 36 through second hooked segment 53. Distal advancement of control member 36 may not, however, apply a force onto second hooked segment 53 sufficient to bend or deflect second arm 51, since some slack may occur in control member 36. Control member 36 may be pushed through second hooked segment 53 without pulling down on second arm 51.

Moreover, second arm 51 may maintain some tension along control member 36 as control member 35 is proximally retracted. Because second arm 51 may remain in the normal configuration, the path of control member 36 may be maintained above longitudinal axis 16 of elongate member 3, and control member 36 may be held substantially taut against second hooked segment 53. When desired, elongate member 3 may be deflected back to the linear configuration shown in FIG. 2 by rotating the knob counterclockwise.

In accordance with the second embodiment, second arm 51 may resiliently deflect towards the normal configuration when distal portion 5 of elongate member 3 is steered to the second direction. Rotating the knob clockwise may proximally retract control member 35 and distally advance control member 36 through second hooked segment 53. Proximal retraction of control member 35 may further deflect first arm 50 downward towards longitudinal axis 16, while distal advancement of control member 36 may release some of the force applied on second arm 51 by control member 36. The slight release in force may cause second arm 51 to resiliently deflect back towards the normal configuration. It should be appreciated that second arm 51 may deflect to the normal configuration or any position between the normal configuration and the slightly bent configuration discussed above.

While second arm 51 may deflect towards the normal configuration, second arm 51 may retain the path of control member 36 above longitudinal axis 16 of elongate member 3 such that tension along control member 36 may be maintained. Moreover, control member 36 may be held substantially taut against second hooked segment 53.

It should be appreciated that first and second arms 50, 51 may be incrementally bent as elongate member 3 is incrementally deflected from the linear configuration. For example, as the knob of actuator 14 is gradually turned counterclockwise, second arm 51 may gradually bend towards longitudinal axis 16 of elongate member 3, and distal portion 5 of elongate member 3 may be gradually steered towards the first direction. Likewise, as the knob of actuator 14 is gradually turned clockwise, first arm 50 may gradually bend towards longitudinal axis 16 of elongate member 3, and distal portion 5 of elongate member 3 may be gradually steered towards the second direction. In certain embodiments, actuator 14 may also include a suitable lock system configured to lock elongate member 3 in a desired linear or deflected position. The lock system may include, for example, a suitable mechanism configured to prevent rotation of the knob, and in turn, lock the linear or deflected position of elongate member 3.

Although not illustrated, it should be appreciated that endoscope 1 may include one or more additional control member holding mechanisms to retain and apply tension to any additional control members. For example, another holding mechanism may be connected to handle housing 10 opposite holding mechanism 39 show in FIGS. 2, 4, and 5, and may retain control members configured to deflect elongate member 3 side-to-side relative to longitudinal axis 16.

It should also be appreciated that in certain embodiments, first and second hooked segments 52, 53 may include a coating of a suitable material configured to reduce friction between first and second hooked segments 52, 53 and control members 35, 36. For example, first and second hooked segments 52, 53 may be coated with a lubricious material, such as, for example, polytetrafluoroethylene, to reduce friction and wear as control members 35, 36 are proximally retracted and distally advanced over first and second hooked segments 52, 53.

Holding mechanism 39 may provide a number of features. For example, first and second arms 50, 51 may maintain tension across control members 35, 36 as either of control member 35 or control member 36 is proximally retracted to steer elongate member 3. By maintaining tension across control members 35, 36, holding mechanism 39 may prevent control members 35, 36 from becoming slacked, thus restricting uncontrolled movement within handle housing 10 and/or elongate member 3. As such, damage to control members 35, 36 and/or other components within endoscope 1 caused by, for example, inadvertent contact and/or snagging of control members 35, 36, may be avoided.

Any aspect set forth in any embodiment may be used with any other embodiment set forth herein. Every device and apparatus set forth herein may be used in any suitable medical procedure, may be advanced through any suitable body lumen and body cavity, and may be used to access tissue from any suitable body portion. For example, the apparatuses and methods described herein may be used through any natural body lumen or tract, including those accessed orally, vaginally, rectally, nasally, urethrally, or through incisions in any suitable tissue.

It will be apparent to those skilled in the art that various modifications and variations can be made in the disclosed devices and processes without departing from the scope of the disclosure. Other embodiments of the disclosure will be apparent to those skilled in the art from consideration of the specification and practice of the disclosure disclosed herein. It is intended that the specification and examples be considered as exemplary only.

What is claimed is:

1. A method, comprising:
using an actuator disposed on a handle of a medical device to move a first control member, wherein the handle includes a holding mechanism, wherein the holding mechanism has a first arm having a first hooked segment and a second arm having a second hooked segment, wherein a connecting segment extends between the first arm and the second arm, wherein the first arm, the second arm, and the connecting segment are together formed of a single, unitary piece of material, wherein the first control member passes through the first hooked segment, and wherein the movement of the first control member causes the first arm to bend away from the connecting segment.

2. The method of claim 1, further comprising:
using the actuator to move a second control member, wherein the second control member passes through the second hooked segment, and wherein the movement of the second control member causes the second arm to bend away from the connecting segment.

3. The method of claim 1, wherein each of the movement of the first control member and the movement of the second control member steers a distal tip of an insertion member extending from the handle, wherein the distal tip is positioned within a body lumen of a patient.

4. The method of claim 1, wherein the first arm applies tension to the first control member, and the second arm applies tension to the second control member.

5. The method of claim 4, wherein the first arm is configured to apply the tension to the first control member by deflecting a path of the first control member, and wherein the second arm is configured to apply the tension to the second control member by deflecting a path of the second control member.

6. The method of claim 1, wherein a proximal end of each of the first and the second control members is connected to a spool, and wherein the holding mechanism is not coaxial with the spool.

7. The method of claim 1, wherein, when the holding mechanism is in a naturally biased state, the first arm is transverse to the second arm.

8. A method, comprising:
moving a first control member in order to steer a distal tip of an insertion portion of a medical device in a first direction, wherein the first control member passes through a first hooked segment of a first arm of a holding mechanism; and
moving a second control member in order to steer the distal tip in a second direction, wherein the second control member passes through a second hooked segment of a second arm of the holding mechanism;
wherein a connecting segment extends between the first arm and the second arm, wherein the movement of the first control member causes the first arm to bend away from the connecting segment, and wherein movement of the second control member causes the second arm to bend away from the connecting segment.

9. The method of claim 8, wherein the first arm, the second arm, and the connecting segment are formed from a single, unitary piece of material.

10. The method of claim 8, wherein the first arm applies tension to the first control member, and the second arm applies tension to the second control member.

11. The method of claim 10, wherein the first arm is configured to apply the tension to the first control member by deflecting a path of the first control member, and wherein the second arm is configured to apply the tension to the second control member by deflecting a path of the second control member.

12. The method of claim 8, wherein a proximal end of each of the first and the second control members is connected to a spool, and wherein the holding mechanism is not coaxial with the spool.

13. The method of claim 8, wherein, when the holding mechanism is in a naturally biased state, the first arm is transverse to the second arm.

14. The method of claim 8, wherein, when the first control member is moved proximally, the first control member moves through the hooked segment in a proximal direction.

15. A method, comprising:
using an actuator of an endoscope handle to move a first control member, wherein the first control member passes through a first hooked segment of a first arm of a holding mechanism, and wherein the holding mechanism further includes a second arm having a second hooked segment and a connecting segment extending between the first arm and the second arm;
bending the first arm away from the connecting segment;
using the actuator to move a second control member, wherein the second control member passes through the second hooked segment; and
bending the second arm away from the connecting segment.

16. The method of claim 15, wherein the movement of the first control member causes the bending of the first arm, and wherein the movement of the second control member causes the bending of the second arm.

17. The method of claim 15, wherein the first arm, the second arm, and the connecting segment are formed from a single, unitary piece of material.

18. The method of claim 15, wherein the first arm applies tension to the first control member, and the second arm applies tension to the second control member.

19. The method of claim 18, wherein the first arm is configured to apply the tension to the first control member by deflecting a path of the first control member, and wherein the second arm is configured to apply the tension to the second control member by deflecting a path of the second control member.

20. The method of claim 15, wherein, when the holding mechanism is in a naturally biased state, the first arm is transverse to the second arm.

* * * * *